US006610537B2

(12) United States Patent
Turner, Jr. et al.

(10) Patent No.: US 6,610,537 B2
(45) Date of Patent: Aug. 26, 2003

(54) HUMAN KINASES AND POLYNUCLEOTIDES ENCODING THE SAME

(75) Inventors: C. Alexander Turner, Jr., The Woodlands, TX (US); Brian Mathur, The Woodlands, TX (US)

(73) Assignee: Lexicon Genetics Incorporated, The Woodlands, TX (US)

(*) Notice: Subject to any disclaimer, the term of this patent is extended or adjusted under 35 U.S.C. 154(b) by 0 days.

(21) Appl. No.: 10/217,357

(22) Filed: Aug. 9, 2002

(65) Prior Publication Data

US 2003/0023063 A1 Jan. 30, 2003

Related U.S. Application Data

(63) Continuation of application No. 09/975,326, filed on Oct. 11, 2001, now Pat. No. 6,476,210
(60) Provisional application No. 60/239,821, filed on Oct. 12, 2000.

(51) Int. Cl.$^7$ .............................. C12N 9/12; C12N 1/26; C12N 15/00; C07H 21/04
(52) U.S. Cl. ............... 435/325; 435/252.3; 435/252.33; 435/194; 435/320.1; 536/23.2
(58) Field of Search .............................. 435/194, 252.3, 435/252.33, 320.1, 325; 536/23.2

(56) References Cited

U.S. PATENT DOCUMENTS

| | | |
|---|---|---|
| 4,215,051 A | 7/1980 | Schroeder et al. |
| 4,376,110 A | 3/1983 | David et al. |
| 4,594,595 A | 6/1986 | Struckman |
| 4,631,211 A | 12/1986 | Houghten |
| 4,689,405 A | 8/1987 | Frank et al. |
| 4,713,326 A | 12/1987 | Dattagupta et al. |
| 4,873,191 A | 10/1989 | Wagner et al. |
| 4,946,778 A | 8/1990 | Ladner et al. |
| 5,252,743 A | 10/1993 | Barrett et al. |
| 5,272,057 A | 12/1993 | Smulson et al. |
| 5,424,186 A | 6/1995 | Fodor et al. |
| 5,445,934 A | 8/1995 | Fodor et al. |
| 5,459,127 A | 10/1995 | Felgner et al. |
| 5,556,752 A | 9/1996 | Lockhart et al. |
| 5,700,637 A | 12/1997 | Southern |
| 5,723,326 A | 3/1998 | Kauffman et al. |
| 5,744,305 A | 4/1998 | Fodor et al. |
| 5,830,721 A | 11/1998 | Stemmer et al. |
| 5,837,458 A | 11/1998 | Minshull et al. |
| 5,869,336 A | 2/1999 | Meyer et al. |
| 5,877,397 A | 3/1999 | Lonberg et al. |
| 5,948,767 A | 9/1999 | Scheule et al. |
| 6,013,455 A | 1/2000 | Bandman et al. |
| 6,075,181 A | 6/2000 | Kucherlapati et al. |
| 6,110,490 A | 8/2000 | Thierry |
| 6,117,679 A | 9/2000 | Stemmer |
| 6,150,584 A | 11/2000 | Kucherlapati et al. |

FOREIGN PATENT DOCUMENTS

| | | |
|---|---|---|
| EP | 0 918 091 A | 5/1999 |
| EP | 0 978 562 A | 2/2000 |
| WO | WO 98 45436 A | 10/1998 |
| WO | WO 00 73469 A | 12/2000 |
| WO | WO 02 16588 A | 2/2002 |

OTHER PUBLICATIONS

Bird et al, 1988, "Single–Chain Antigen–Binding Proteins", Science 242:423–426.

Bitter et al, 1987, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Gautier et al, 1987, "α–DNA IV:α–anomeric and β–anomeric tetrathymidylates covalently linked to inercalating oxazolopyridocarbazole. Synthesis, physiochemical properties and poly (rA) binding", Nucleic Acids Research 15(16):6625–6641.

Gordon, 1989, "Transgenic Animals", International Review of Cytology, 115:171–229.

Greenspan et al, 1993, "Idiotypes: structure and immunogenicity", FASEB Journal 7:437–444.

Gu et al, 1994, "Deletion of a DNA Polymerase β Gene Segment in T Cells Using Cell Type–Specific Gene Targeting", Science 265:103–106.

Huse et al, 1989, "Generation of a Large Combinatorial Library of the Immunoglobulin Repertoire in Phage Lambda", Science 246:1275–1281.

Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.

Inoue et al, 1987, "Sequence–dependent hydrolysis of RNA using modified oligonucleotide splints and R Nase H", FEBS Letters 215(2):327–330.

Inoue et al, 1987, "Synthesis and hybridization studies on two complementary nona(2'–O–methyl)ribonucleotides", Nucleic Acids Research 15(15):6131–6149.

Inouye & Inouye, 1985, "Up–promoter mutations in the Ipp gene of *Escherichia coli*", Nucleic Acids Research 13(9):3101–3110.

(List continued on next page.)

*Primary Examiner*—Rebecca E. Prouty
*Assistant Examiner*—Sheridan L. Swope

(57) ABSTRACT

Human polynucleotide and polypeptide sequences for novel protein kinases are disclosed that can be used in therapeutic, diagnostic, and pharmacogenomic applications.

6 Claims, No Drawings

OTHER PUBLICATIONS

Janknecht et al, 1991, "Rapid and efficient purification of native histidine–tagged protein expressed by recombinant vaccinia virus", PNAS 88:8972–8976.

Kohler & Milstein, 1975, "Continuous cultures of fused cells secreting antibody of predefined specificity", Nature 256:495–497.

Lakso et al, 1992, "Targeted oncogene activation by site–specific recombination in transgenic mice", Proc. Natl. Acad. Sci. USA 89:6232–6236.

Lavitrano et al, 1989, "Sperm Cells as Vectors for Introducing Foreign DNA into Eggs: Genetic Transformation of Mice", Cell 57:717–723.

Lo, 1983, "Transformation by Iontophoretic Microinjection of DNA: Multiple Integrations without Tandem Insertions", Mol. & Cell. Biology 3(10):1803–1814.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

HUMAN KINASES AND POLYNUCLEOTIDES ENCODING THE SAME

The present application is a continuation of U.S. application Ser. No. 09/975,326, filed Oct. 11, 2001 now U.S. Pat. No. 6,476,210, which claims the benefit of U.S. Provisional Application No. 60/239,821 which was filed on Oct. 12, 2000, each of which are herein incorporated by reference in their entirety.

1. INTRODUCTION

The present invention relates to the discovery, identification, and characterization of novel human polynucleotides encoding proteins sharing sequence similarity with animal kinases. The invention encompasses the described polynucleotides, host cell expression systems, the encoded proteins, fusion proteins, polypeptides and peptides, antibodies to the encoded proteins and peptides, and genetically engineered animals that either lack or over express the disclosed genes, antagonists and agonists of the proteins, and other compounds that modulate the expression or activity of the proteins encoded by the disclosed genes that can be used for diagnosis, drug screening, clinical trial monitoring, the treatment of diseases and disorders, and cosmetic or nutriceutical applications.

2. BACKGROUND OF THE INVENTION

Kinases mediate the phosphorylation of a wide variety of proteins and compounds in the cell. Along with phosphatases, kinases are involved in a range of regulatory pathways. Given the physiological importance of kinases, they have been subject to intense scrutiny and are proven drug targets.

3. SUMMARY OF THE INVENTION

The present invention relates to the discovery, identification, and characterization of nucleotides that encode novel human proteins and the corresponding amino acid sequences of these proteins. The novel human proteins (NHPs) described for the first time herein share structural similarity with animal kinases, including, but not limited to, serine-threonine kinases, calcium/calmodulin-dependent protein kinases, and mitogen activated kinases. Accordingly, the described NHPs encode novel kinases having homologues and orthologs across a range of phyla and species.

The novel human polynucleotides described herein, encode open reading frames (ORFs) encoding proteins of 766 and 765 amino acids in length (see respectively SEQ ID NOS: 2 and 4).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and open reading frame or regulatory sequence replacement constructs) or to enhance the expression of the described NHPs (e.g., expression constructs that place the described polynucleotide under the control of a strong promoter system), and transgenic animals that express a NHP sequence, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–4 are "knocked-out" they provide a method of identifying phenotypic expression of the particular gene as well as a method of assigning function to previously unknown genes. In addition, animals in which the unique NHP sequences described in SEQ ID NOS:1–4 are "knocked-out" provide a unique source in which to elicit antibodies to homologous and orthologous proteins that would have been previously viewed by the immune system as "self" and therefore would have failed to elicit significant antibody responses. To these ends, gene trapped knockout ES cells have been generated in murine homologs of the described NHPs.

Additionally, the unique NHP sequences described in SEQ ID NOS:1–4 are useful for the identification of protein coding sequence and mapping a unique gene to a particular chromosome. These sequences identify biologically verified exon splice junctions as opposed to splice junctions that may have been bioinformatically predicted from genomic sequence alone. The sequences of the present invention are also useful as additional DNA markers for restriction fragment length polymorphism (RFLP) analysis, and in forensic biology.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequence of the novel human ORFs encoding the described novel human kinase proteins.

5. DETAILED DESCRIPTION OF THE INVENTION

The NHPs described for the first time herein are novel proteins that are expressed in, inter alia, human cell lines and human fetal brain, brain, pituitary, spinal cord, testis, adipose, and esophagus cells. The described sequences were compiled from sequences available in GENBANK, and cDNAs generated from skeletal muscle, adipose, pituitary, cerebellum, and brain mRNA (Edge Biosystems, Gaithersburg, Md.).

The present invention encompasses the nucleotides presented in the Sequence Listing, host cells expressing such nucleotides, the expression products of such nucleotides, and: (a) nucleotides that encode mammalian homologs of the described genes, including the specifically described NHPs, and the NHP products; (b) nucleotides that encode one or more portions of an NHP that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor/ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing. As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1× SSC/0.1% SDS at 68° C. (Ausubel et al., eds., 1989, Current Protocols in Molecular Biology, Vol. I, Green Publishing Associates, Inc., and John Wiley & sons, Inc., New York, at p. 2.10.3) and encodes a functionally equivalent expression product. Additionally, contemplated are any nucleotide sequences that hybridize to the complement of the DNA sequence that encode and express an amino acid sequence presented in the Sequence Listing under moderately stringent conditions, e.g., washing in 0.2× SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458 or 5,723,323, both of which are herein incorporated by reference). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar to corresponding regions of SEQ ID NO:1 (as measured by BLAST sequence comparison analysis using, for example, the GCG sequence analysis package using default parameters).

The invention also includes nucleic acid molecules, preferably DNA molecules, that hybridize to, and are therefore the complements of, the described NHP encoding polynucleotides. Such hybridization conditions can be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–4 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–4, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the-disclosures of which are herein incorporated by reference in their entirety.

Addressable arrays comprising sequences first disclosed in SEQ ID NOS:1–4 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–4.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–4 provides detailed information about transcriptional changes involved in a specific pathway, potentially leading to the identification of novel components or gene functions that manifest themselves as novel phenotypes.

Probes consisting of sequences first disclosed in SEQ ID NOS:1–4 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–4 can be utilized in microarrays or other assay formats, to screen collections of genetic material from patients who have a particular medical condition. These investigations can also be carried out using the sequences first disclosed in SEQ ID NOS:1–4 in silico and by comparing previously collected genetic databases and the disclosed sequences using computer software known to those in the art.

Thus the sequences first disclosed in SEQ ID NOS:1–4 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–4. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6× SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences can be used as part of ribozyme and/or triple helix sequences that are also useful for NHP gene regulation.

Inhibitory antisense or double stranded oligonucleotides can additionally comprise at least one modified base moiety that is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, supra.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

For example, the present sequences can be used in restriction fragment length polymorphism (RFLP) analysis to identify specific individuals. In this technique, an individual's genomic DNA is digested with one or more restriction enzymes, and probed on a Southern blot to yield unique bands for identification (as generally described in U.S. Pat. No. 5,272,057, incorporated herein by reference). In addition, the sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). Actual base sequence information can be used for identification as an accurate alternative to patterns formed by restriction enzyme generated fragments.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from, for example, human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, immune disorders, obesity, high blood pressure, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue may be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor.) Additionally, screening can be accomplished by screening with labeled NHP fusion proteins, such as, for example, alkaline phosphatase-NHP or NHP-alkaline phosphatase fusion proteins. In cases where a NHP mutation results in an expression product with altered function (e.g., as a result of a missense or a frameshift mutation), polyclonal antibodies to NHP are likely to cross-react with a corresponding mutant NHP expression product. Library clones detected via their reaction with such labeled antibodies can be purified and subjected to sequence analysis according to methods well known in the art.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721, 5,837,458, 6,117,679, and 5,723,323, which are herein incorporated by reference in their entirety.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculovirus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP sequence under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

Where, as in the present instance, some of the described NHP peptides or polypeptides are thought to be cytoplasmic or nuclear proteins (although processed forms or fragments can be secreted- or membrane associated), expression systems can be engineered that produce soluble derivatives of a NHP (corresponding to a NHP extracellular and/or intracellular domains, or truncated polypeptides lacking one or more hydrophobic domains) and/or NHP fusion protein products (especially NHP-Ig fusion proteins, i.e., fusions of a NHP domain to an IgFc), NHP antibodies, and anti-idiotypic antibodies (including Fab fragments) that can be used in therapeutic applications. Preferably, the above expression systems are engineered to allow the desired peptide or polypeptide to be recovered from the culture media.

The present invention also encompasses antibodies and anti-idiotypic antibodies (including Fab fragments), antagonists and agonists of a NHP, as well as compounds or nucleotide constructs that inhibit expression of a NHP sequence (transcription factor inhibitors, antisense and ribozyme molecules, or open reading frame sequence or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a NHP in the body. The use of engineered host cells and/or animals can offer an advantage in that such systems allow not only for the identification of compounds that bind to the endogenous receptor/ligand of a NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP or a protein interactive therewith. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and corresponding deduced amino acid sequences of the described NHPs are presented in the Sequence Listing.

Expression analysis has provided evidence that the described NHPs can be expressed in a relatively narrow range of human tissues. In addition to serine-threonine kinases, the described NHPs also share significant similarity to a range of additional kinase families, including kinases associated with signal transduction, from a variety of phyla and species.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458, which are herein incorporated by reference in their entirety.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHP transgene in all their cells, as well as animals that carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such a cell-type specific activation will depend upon the particular cell type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell type, thus inactivating the endogenous NHP gene in only that cell type, by following, for example, the teaching of Gu et al., 1994, Science, 265:103–106. The regulatory sequences required for such a cell-type specific inactivation will depend upon the particular cell type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include but are not limited to Northern blot analysis of tissue samples obtained from the animal, in situ hybridization analysis, and RT-PCR. Samples of NHP gene-expressing tissue, may also be evaluated immunocytochemically using antibodies specific for the NHP transgene product.

5.2 NHPS and NHP Polypeptides

NHPs, NHP polypeptides, NHP peptide fragments, mutated, truncated, or deleted forms of the NHPs, and/or NHP fusion proteins can be prepared for a variety of uses. These uses include, but are not limited to, the generation of antibodies, as reagents in diagnostic assays, for the identification of other cellular gene products related to a NHP, as reagents in assays for screening for compounds that can be used as pharmaceutical reagents useful in the therapeutic treatment of mental, biological, or medical disorders and disease. Given the similarity information and expression data, the described NHPs can be targeted (by drugs, oligos, antibodies, etc.) in order to treat disease, or to therapeutically augment the efficacy of therapeutic agents.

The Sequence Listing discloses the amino acid sequences encoded by the described NHP-encoding polynucleotides. The NHPs display initiator methionines that are present in DNA sequence contexts consistent with eucaryotic translation initiation sites. The NHPs do not display consensus signal sequences, which indicates that they may be cytoplasmic or possibly nuclear proteins, although they may also be secreted or membrane associated.

The NHP amino acid sequences of the invention include the amino acid sequences presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al., eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and modify a NHP substrate, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but that result in a silent change, thus producing a functionally equivalent expression product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where the NHP peptide or polypeptide can exist, or has been engineered to exist, as a soluble or secreted molecule, the soluble NHP peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target expression product can be released from the GST moiety.

In an insect system, *Autographa californica* nuclear polyhedrosis virus (AcNPV) is used as a vector to express foreign polynucleotide sequences. The virus grows in *Spodoptera frugiperda* cells. A NHP coding sequence can be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., see Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the expression product in the specific fashion desired. Such modifications (e.g., glycosylation) and processing (e.g., cleavage) of protein products may be important for the function of the protein. Different host cells have characteristic and specific mechanisms for the post-translational processing and modification of proteins and expression products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the expression product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines that stably express the NHP sequences described above can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines that express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes, which can be employed in tk⁻, hgprt⁻ or aprt⁻ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al., allows for the ready purification of non-denatured fusion proteins expressed in human cell lines (Janknecht, et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto $Ni^{2+}$-nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in "Liposomes: A Practical Approach", New, ed., Oxford University Press, New York and in U.S. Pat. Nos. 4,594,595, 5,459,127, 5,948,767 and 6,110,490 and their respective disclosures, which are herein incorporated by reference in their entirety. Additionally embodied are novel protein constructs engineered in such a way that they facilitate transport of the NHP to the target site or desired organ, where they cross the cell membrane and/or the nucleus where the NHP can exert its functional activity. This goal may be achieved by coupling of the NHP to a cytokine or other ligand that provides targeting specificity, and/or to a protein transducing domain (see generally U.S. applications Ser. Nos. 60/111,701 and 60/056,713, both of which are herein incorporated by reference, for examples of such transducing sequences) to facilitate passage across cellular membranes and can optionally be engineered to include nuclear localization.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention can be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP expression product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, a NHP peptide (e.g., one corresponding to a functional domain of a NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diphtheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique that provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures, which are herein incorporated by reference in their entirety. Also encompassed by the present invention is the use of fully humanized monoclonal antibodies as described in U.S. Pat. No. 6,150,584 and respective disclosures, which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP expression products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include, but are not limited to: the F(ab')$_2$ fragments, which can be produced by pepsin digestion of the antibody molecule and the Fab fragments, which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies that bind to a NHP domain and competitively inhibit the binding of NHP to its cognate receptor/ligand can be used to generate anti-idiotypes that "mimic" the NHP and, therefore, bind, activate, or neutralize a NHP, NHP receptor, or NHP ligand. Such anti-idiotypic antibodies or Fab fragments of such anti-idiotypes can be used in therapeutic regimens involving a NHP mediated pathway.

Additionally given the high degree of relatedness of mammalian NHPs, the presently described knock-out mice (having never seen NHP, and thus never been tolerized to NHP) have a unique utility, as they can be advantageously applied to the generation of antibodies against the disclosed mammalian NHP (i.e., NHP will be immunogenic in NHP knock-out animals).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. A recombinant expression vector comprising an isolated nucleic acid molecule that encodes the amino acid sequence shown in SEQ ID NO:2.

2. The recombinant expression vector of claim 1, wherein said isolated nucleic acid molecule comprises the nucleic acid sequence of SEQ ID NO:1.

3. A host cell comprising the vector of claim 1.

4. A recombinant expression vector comprising an isolated nucleic acid molecule that encodes the amino acid sequence shown in SEQ ID NO:4.

5. The recombinant expression vector of claim 4, wherein said isolated nucleic acid molecule comprises the nucleic acid sequence of SEQ ID NO:2.

6. A host cell comprising the vector of claim 4.

* * * * *

SEQUENCE LISTING

<160> NUMBER OF SEQ ID NOS: 4

<210> SEQ ID NO 1
<211> LENGTH: 2301
<212> TYPE: DNA
<213> ORGANISM: homo sapiens

<400> SEQUENCE: 1

| | | | | | |
|---|---|---|---|---|---|
| atggccagca | ccaggagtat | cgagctggag | cactttgagg | aacgggacaa | aaggccgcgg | 60 |
| ccggggtcgc | ggagaggggc | ccccagctcc | tccgggggca | gcagcagctc | gggccccaag | 120 |
| gggaacgggc | tcatcccag | tccggcgcac | agtgcccact | gcagcttcta | ccgcacgcgg | 180 |
| accctgcagg | ccctcagctc | ggagaagaag | gccaagaagg | cgcgcttcta | ccggaacggg | 240 |
| gaccgctact | tcaagggcct | ggtgtttgcc | atctccagcg | accgcttccg | gtcyttcgat | 300 |
| gcgctcctca | tagagctcac | ccgctccctg | tcggacaacg | tgaacctgcc | ccagggtgtc | 360 |
| cgcactatct | acaccatcga | cggcagccgg | aaggtcacca | gcctggacga | gctgctggaa | 420 |
| ggtgagagtt | acgtgtgtgc | atccaatgaa | ccatttcgta | aagtcgatta | caccaaaaat | 480 |
| attaatccaa | actggtctgt | gaacatcaag | ggtgggacat | cccgagcgct | ggctgctgcc | 540 |
| tcctctgtga | aaagtgaagt | aaaagaaagt | aaagatttca | tcaaacccaa | gttagtgact | 600 |
| gtgattcgaa | gtggagtgaa | gcctagaaaa | gccgtgcgga | tccttctgaa | taaaaagact | 660 |
| gctcattcct | ttgaacaagt | cttaacagat | atcaccgaag | ccattaaact | agactcagga | 720 |
| gtcgtcaaga | ggctctgcac | cctggatgga | aagcaggtta | cttgtctgca | agacttttt | 780 |
| ggtgatgacg | atgtttttat | tgcatgtgga | ccagaaaaat | ttcgttatgc | caagatgac | 840 |
| tttgtcctgg | atcatagtga | atgtcgtgtc | ctgaagtcat | cttattctcg | atcctcagct | 900 |
| gttaagtatt | ctggatccaa | aagccctggg | ccctctcgac | gcagcaaatc | accagcttca | 960 |
| gttaatggaa | ctcccagcag | ccaactttct | actcctaaat | ctacgaaatc | ctccagttcc | 1020 |
| tctccaacta | gtccaggaag | tttcagagga | ttaaagcaga | tttctgctca | tggcagatct | 1080 |
| tcttccaatg | taaacggtgg | acctgagctt | gaccgttgca | taagtcctga | aggtgtgaat | 1140 |
| ggaaacagat | gctctgaatc | atcaactctt | cttgagaaat | acaaaattgg | aaaggtcatt | 1200 |
| ggtgatggca | atttttgcagt | agtcaaagag | tgtatagaca | ggtccactgg | aaaggagttt | 1260 |
| gccctaaaga | ttatagacaa | agccaaatgt | tgtggaaagg | aacacctgat | tgagaatgaa | 1320 |
| gtgtcaatac | tgcgccgagt | gaaacatccc | aatatcatta | tgctggtcga | ggagatggaa | 1380 |
| acagcaactg | agctctttct | ggtgatggaa | ttggtcaaag | gtggagatct | ctttgatgca | 1440 |
| attacttcgt | cgaccaagta | cactgagaga | gatggcagtg | ccatggtgta | caacttagcc | 1500 |
| aatgccctca | ggtatctcca | tggcctcagc | atcgtgcaca | gagacatcaa | accagagaat | 1560 |
| ctcttggtgt | gtgaatatcc | tgatggaacc | aagtctttga | aactgggaga | ctttgggctt | 1620 |
| gcgactgtgg | tagaaggccc | tttatacaca | gtctgtggca | cacccactta | tgtggctcca | 1680 |
| gaaatcattg | ctgaaactgg | ctatggcctg | aaggtggaca | tttgggcagc | tggtgtgatc | 1740 |
| acatacatac | ttctctgtgg | attcccacca | ttccgaagtg | agaacaatct | ccaggaagat | 1800 |
| ctcttcgacc | agatcttggc | tgggaagctg | gagtttccgg | cccctactg | ggataacatc | 1860 |
| acggactctg | ccaaggaatt | aatcagtcaa | atgcttcagg | taaatgttga | agctcggtgt | 1920 |
| accgcgggac | aaatcctgag | tcacccctgg | gtgtcagatg | atgcctccca | ggagaataac | 1980 |
| atgcaagctg | aggtgacagg | taaactaaaa | cagcacttta | ataatgcgct | ccccaaacag | 2040 |

```
aacagcacta ccaccggggt ctccgtcatc atgaacacgg ctctagataa ggaggggcag   2100
attttctgca gcaagcactg tcaagacagc ggcaggcctg ggatggagcc catctctcca   2160
gttcctccct cagtggagga gatccctgtg cctggggaag cagtcccggc ccccaccoct   2220 ccggaatctc ccaccccca ctgtcctccc gctgccccgg gtggtgagcg ggcaggaacc   2280
tggcgccgcc accgagactg a                                            2301
```

<210> SEQ ID NO 2
<211> LENGTH: 766
<212> TYPE: PRT
<213> ORGANISM: homo sapiens

<400> SEQUENCE: 2

```
Met Ala Ser Thr Arg Ser Ile Glu Leu Glu His Phe Glu Glu Arg Asp
 1               5                  10                  15

Lys Arg Pro Arg Pro Gly Ser Arg Gly Ala Pro Ser Ser Ser Gly
            20                  25                  30

Gly Ser Ser Ser Gly Pro Lys Gly Asn Gly Leu Ile Pro Ser Pro
        35                  40                  45

Ala His Ser Ala His Cys Ser Phe Tyr Arg Thr Arg Thr Leu Gln Ala
 50                  55                  60

Leu Ser Ser Glu Lys Lys Ala Lys Ala Arg Phe Tyr Arg Asn Gly
 65                  70                  75              80

Asp Arg Tyr Phe Lys Gly Leu Val Phe Ala Ile Ser Ser Asp Arg Phe
            85                  90                  95

Arg Ser Phe Asp Ala Leu Leu Ile Glu Leu Thr Arg Ser Leu Ser Asp
            100                 105                 110

Asn Val Asn Leu Pro Gln Gly Val Arg Thr Ile Tyr Thr Ile Asp Gly
        115                 120                 125

Ser Arg Lys Val Thr Ser Leu Asp Glu Leu Leu Glu Gly Glu Ser Tyr
        130                 135                 140

Val Cys Ala Ser Asn Glu Pro Phe Arg Lys Val Asp Tyr Thr Lys Asn
145                 150                 155                 160

Ile Asn Pro Asn Trp Ser Val Asn Ile Lys Gly Gly Thr Ser Arg Ala
            165                 170                 175

Leu Ala Ala Ala Ser Ser Val Lys Ser Glu Val Lys Glu Ser Lys Asp
            180                 185                 190

Phe Ile Lys Pro Lys Leu Val Thr Val Ile Arg Ser Gly Val Lys Pro
        195                 200                 205

Arg Lys Ala Val Arg Ile Leu Leu Asn Lys Lys Thr Ala His Ser Phe
    210                 215                 220

Glu Gln Val Leu Thr Asp Ile Thr Glu Ala Ile Lys Leu Asp Ser Gly
225                 230                 235                 240

Val Val Lys Arg Leu Cys Thr Leu Asp Gly Lys Gln Val Thr Cys Leu
            245                 250                 255

Gln Asp Phe Phe Gly Asp Asp Val Phe Ile Ala Cys Gly Pro Glu
            260                 265                 270

Lys Phe Arg Tyr Ala Gln Asp Asp Phe Val Leu Asp His Ser Glu Cys
        275                 280                 285

Arg Val Leu Lys Ser Ser Tyr Ser Arg Ser Ser Ala Val Lys Tyr Ser
    290                 295                 300

Gly Ser Ser Pro Gly Pro Ser Arg Arg Ser Lys Ser Pro Ala Ser
305                 310                 315                 320
```

-continued

```
Val Asn Gly Thr Pro Ser Ser Gln Leu Ser Thr Pro Lys Ser Thr Lys
            325                 330                 335

Ser Ser Ser Ser Ser Pro Thr Ser Pro Gly Ser Phe Arg Gly Leu Lys
            340                 345                 350

Gln Ile Ser Ala His Gly Arg Ser Ser Asn Val Asn Gly Gly Pro
            355                 360                 365

Glu Leu Asp Arg Cys Ile Ser Pro Glu Gly Val Asn Gly Asn Arg Cys
    370                 375                 380

Ser Glu Ser Ser Thr Leu Leu Glu Lys Tyr Lys Ile Gly Lys Val Ile
385                 390                 395                 400

Gly Asp Gly Asn Phe Ala Val Val Lys Glu Cys Ile Asp Arg Ser Thr
            405                 410                 415

Gly Lys Glu Phe Ala Leu Lys Ile Ile Asp Lys Ala Lys Cys Cys Gly
            420                 425                 430

Lys Glu His Leu Ile Glu Asn Glu Val Ser Ile Leu Arg Arg Val Lys
            435                 440                 445

His Pro Asn Ile Ile Met Leu Val Glu Glu Met Glu Thr Ala Thr Glu
            450                 455                 460

Leu Phe Leu Val Met Glu Leu Val Lys Gly Gly Asp Leu Phe Asp Ala
465                 470                 475                 480

Ile Thr Ser Ser Thr Lys Tyr Thr Glu Arg Asp Gly Ser Ala Met Val
            485                 490                 495

Tyr Asn Leu Ala Asn Ala Leu Arg Tyr Leu His Gly Leu Ser Ile Val
            500                 505                 510

His Arg Asp Ile Lys Pro Glu Asn Leu Leu Val Cys Glu Tyr Pro Asp
            515                 520                 525

Gly Thr Lys Ser Leu Lys Leu Gly Asp Phe Gly Leu Ala Thr Val Val
            530                 535                 540

Glu Gly Pro Leu Tyr Thr Val Cys Gly Thr Pro Thr Tyr Val Ala Pro
545                 550                 555                 560

Glu Ile Ile Ala Glu Thr Gly Tyr Gly Leu Lys Val Asp Ile Trp Ala
            565                 570                 575

Ala Gly Val Ile Thr Tyr Ile Leu Leu Cys Gly Phe Pro Pro Phe Arg
            580                 585                 590

Ser Glu Asn Asn Leu Gln Glu Asp Leu Phe Asp Gln Ile Leu Ala Gly
            595                 600                 605

Lys Leu Glu Phe Pro Ala Pro Tyr Trp Asp Asn Ile Thr Asp Ser Ala
610                 615                 620

Lys Glu Leu Ile Ser Gln Met Leu Gln Val Asn Val Glu Ala Arg Cys
625                 630                 635                 640

Thr Ala Gly Gln Ile Leu Ser His Pro Trp Val Ser Asp Asp Ala Ser
            645                 650                 655

Gln Glu Asn Asn Met Gln Ala Glu Val Thr Gly Lys Leu Lys Gln His
            660                 665                 670

Phe Asn Asn Ala Leu Pro Lys Gln Asn Ser Thr Thr Thr Gly Val Ser
            675                 680                 685

Val Ile Met Asn Thr Ala Leu Asp Lys Glu Gly Gln Ile Phe Cys Ser
            690                 695                 700

Lys His Cys Gln Asp Ser Gly Arg Pro Gly Met Glu Pro Ile Ser Pro
705                 710                 715                 720

Val Pro Pro Ser Val Glu Glu Ile Pro Val Pro Gly Glu Ala Val Pro
            725                 730                 735

Ala Pro Thr Pro Pro Glu Ser Pro Thr Pro His Cys Pro Pro Ala Ala
```

|       |       | 740   |       |       |       | 745   |       |       |       | 750   |       |
|-------|-------|-------|-------|-------|-------|-------|-------|-------|-------|-------|-------|
| Pro   | Gly   | Gly   | Glu   | Arg   | Ala   | Gly   | Thr   | Trp   | Arg   | Arg   | His   | Arg | Asp |
|       |       | 755   |       |       |       | 760   |       |       |       | 765   |       |

<210> SEQ ID NO 3
<211> LENGTH: 2298
<212> TYPE: DNA
<213> ORGANISM: homo sapiens

<400> SEQUENCE: 3

| atggccagca ccaggagtat cgagctggag cactttgagg aacgggacaa aaggccgcgg | 60 |
| ccggggtcgc ggagaggggc ccccagctcc tccgggggca gcagcagctc gggccccaag | 120 |
| gggaacgggc tcatccccag tccggcgcac agtgcccact gcagcttcta ccgcacgcgg | 180 |
| accctgcagg ccctcagctc ggagaagaag gccagaaagg cgcgcttcta ccggaacggg | 240 |
| gaccgctact tcaagggcct ggtgtttgcc atctccagcg accgcttccg gtcyttcgat | 300 |
| gcgctcctca tagagctcac ccgctccctg tcggacaacg tgaacctgcc ccagggtgtc | 360 |
| cgcactatct acaccatcga cggcagccgg aaggtcacca gcctggacga gctgctggaa | 420 |
| ggtgagagtt acgtgtgtgc atccaatgaa ccatttcgta aagtcgatta caccaaaaat | 480 |
| attaatccaa actggtctgt gaacatcaag ggtgggacat cccgagcgct ggctgctgcc | 540 |
| tcctctgtga aaagtgaagt aaaagaaagt aaagatttca tcaaacccaa gttagtgact | 600 |
| gtgattcgaa gtggagtgaa gcctagaaaa gccgtgcgga tccttctgaa taaaaagact | 660 |
| gctcattcct ttgaacaagt cttaacagat atcaccgaag ccattaaact agactcagga | 720 |
| gtcgtcaaga ggctctgcac cctggatgga aagcaggtta cttgtctgca agactttttt | 780 |
| ggtgatgacg atgttttat tgcatgtgga ccagaaaaat ttcgttatgc ccaagatgac | 840 |
| tttgtcctgg atcatagtga atgtcgtgtc ctgaagtcat cttattctcg atcctcagct | 900 |
| gttaagtatt ctggatccaa aagccctggg ccctctcgac gcagcaaatc accagcttca | 960 |
| gttaatggaa ctcccagcag ccaactttct actcctaaat ctacgaaatc ctccagttcc | 1020 |
| tctccaacta gtccaggaag tttcagagga ttaaagattt ctgctcatgg cagatcttct | 1080 |
| tccaatgtaa acgtggacc tgagcttgac cgttgcataa gtcctgaagg tgtgaatgga | 1140 |
| aacagatgct ctgaatcatc aactcttctt gagaaataca aaattggaaa ggtcattggt | 1200 |
| gatggcaatt ttgcagtagt caaagagtgt atagacaggt ccactggaaa ggagtttgcc | 1260 |
| ctaaagatta tagacaaagc caaatgttgt ggaaaggaac acctgattga gaatgaagtg | 1320 |
| tcaatactgc gccgagtgaa acatcccaat atcattatgc tggtcgagga gatgaaaaca | 1380 |
| gcaactgagc tctttctggt gatggaattg gtcaaaggtg gagatctctt tgatgcaatt | 1440 |
| acttcgtcga ccaagtacac tgagagagat ggcagtgcca tggtgtacaa cttagccaat | 1500 |
| gccctcaggt atctccatgg cctcagcatc gtgcacagac atcaaaacc agagaatctc | 1560 |
| ttggtgtgtg aatatcctga tggaaccaag tcttgaaac tgggagactt tgggcttgcg | 1620 |
| actgtggtag aaggcccttt atacacagtc tgtggcacac ccactatgt ggctccagaa | 1680 |
| atcattgctg aaactggcta tggcctgaag gtggacattt gggcagctgg tgtgatcaca | 1740 |
| tacatacttc tctgtggatt cccaccattc cgaagtgaga caatctcca ggaagatctc | 1800 |
| ttcgaccaga tcttggctgg gaagctggag tttccggccc cctactggga taacatcacg | 1860 |
| gactctgcca aggaattaat cagtcaaatg cttcaggtaa atgttgaagc tcggtgtacc | 1920 |
| gcgggacaaa tcctgagtca cccctgggtg tcagatgatg cctcccagga gaataacatg | 1980 |

-continued

```
caagctgagg tgacaggtaa actaaaacag cactttaata atgcgctccc caaacagaac    2040
agcactacca ccggggtctc cgtcatcatg aacacggctc tagataagga ggggcagatt    2100
ttctgcagca agcactgtca agacagcggc aggcctggga tggagcccat ctctccagtt    2160
cctccctcag tggaggagat ccctgtgcct ggggaagcag tcccggcccc caccctccg     2220 gaatctccca cccccactg tcctcccgct gccccgggtg gtgagcgggc aggaacctgg     2280
cgccgccacc gagactga                                                  2298
```

<210> SEQ ID NO 4
<211> LENGTH: 765
<212> TYPE: PRT
<213> ORGANISM: homo sapiens

<400> SEQUENCE: 4

```
Met Ala Ser Thr Arg Ser Ile Glu Leu Glu His Phe Glu Glu Arg Asp
 1               5                  10                  15

Lys Arg Pro Arg Pro Gly Ser Arg Gly Ala Pro Ser Ser Ser Gly
                20                  25                  30

Gly Ser Ser Ser Gly Pro Lys Gly Asn Gly Leu Ile Pro Ser Pro
             35                  40                  45

Ala His Ser Ala His Cys Ser Phe Tyr Arg Thr Arg Thr Leu Gln Ala
         50                  55                  60

Leu Ser Ser Glu Lys Lys Ala Lys Lys Ala Arg Phe Tyr Arg Asn Gly
 65                  70                  75                  80

Asp Arg Tyr Phe Lys Gly Leu Val Phe Ala Ile Ser Ser Asp Arg Phe
                 85                  90                  95

Arg Ser Phe Asp Ala Leu Leu Ile Glu Leu Thr Arg Ser Leu Ser Asp
            100                 105                 110

Asn Val Asn Leu Pro Gln Gly Val Arg Thr Ile Tyr Thr Ile Asp Gly
        115                 120                 125

Ser Arg Lys Val Thr Ser Leu Asp Glu Leu Leu Glu Gly Glu Ser Tyr
    130                 135                 140

Val Cys Ala Ser Asn Glu Pro Phe Arg Lys Val Asp Tyr Thr Lys Asn
145                 150                 155                 160

Ile Asn Pro Asn Trp Ser Val Asn Ile Lys Gly Gly Thr Ser Arg Ala
                165                 170                 175

Leu Ala Ala Ser Ser Val Lys Ser Glu Val Lys Glu Ser Lys Asp
            180                 185                 190

Phe Ile Lys Pro Lys Leu Val Thr Val Ile Arg Ser Gly Val Lys Pro
        195                 200                 205

Arg Lys Ala Val Arg Ile Leu Leu Asn Lys Lys Thr Ala His Ser Phe
    210                 215                 220

Glu Gln Val Leu Thr Asp Ile Thr Glu Ala Ile Lys Leu Asp Ser Gly
225                 230                 235                 240

Val Val Lys Arg Leu Cys Thr Leu Asp Gly Lys Gln Val Thr Cys Leu
                245                 250                 255

Gln Asp Phe Phe Gly Asp Asp Asp Val Phe Ile Ala Cys Gly Pro Glu
            260                 265                 270

Lys Phe Arg Tyr Ala Gln Asp Asp Phe Val Leu Asp His Ser Glu Cys
        275                 280                 285

Arg Val Leu Lys Ser Ser Tyr Ser Arg Ser Ala Val Lys Tyr Ser
    290                 295                 300

Gly Ser Lys Ser Pro Gly Pro Ser Arg Arg Ser Lys Ser Pro Ala Ser
305                 310                 315                 320
```

```
Val Asn Gly Thr Pro Ser Ser Gln Leu Ser Thr Pro Lys Ser Thr Lys
                325                 330                 335

Ser Ser Ser Ser Ser Pro Thr Ser Pro Gly Ser Phe Arg Gly Leu Lys
            340                 345                 350

Ile Ser Ala His Gly Arg Ser Ser Asn Val Asn Gly Gly Pro Glu
        355                 360                 365

Leu Asp Arg Cys Ile Ser Pro Glu Gly Val Asn Gly Asn Arg Cys Ser
        370                 375                 380

Glu Ser Ser Thr Leu Leu Glu Lys Tyr Lys Ile Gly Lys Val Ile Gly
385                 390                 395                 400

Asp Gly Asn Phe Ala Val Val Lys Glu Cys Ile Asp Arg Ser Thr Gly
                405                 410                 415

Lys Glu Phe Ala Leu Lys Ile Ile Asp Lys Ala Lys Cys Cys Gly Lys
                420                 425                 430

Glu His Leu Ile Glu Asn Glu Val Ser Ile Leu Arg Arg Val Lys His
            435                 440                 445

Pro Asn Ile Ile Met Leu Val Glu Glu Met Glu Thr Ala Thr Glu Leu
        450                 455                 460

Phe Leu Val Met Glu Leu Val Lys Gly Gly Asp Leu Phe Asp Ala Ile
465                 470                 475                 480

Thr Ser Ser Thr Lys Tyr Thr Glu Arg Asp Gly Ser Ala Met Val Tyr
                485                 490                 495

Asn Leu Ala Asn Ala Leu Arg Tyr Leu His Gly Leu Ser Ile Val His
            500                 505                 510

Arg Asp Ile Lys Pro Glu Asn Leu Leu Val Cys Glu Tyr Pro Asp Gly
            515                 520                 525

Thr Lys Ser Leu Lys Leu Gly Asp Phe Gly Leu Ala Thr Val Val Glu
        530                 535                 540

Gly Pro Leu Tyr Thr Val Cys Gly Thr Pro Thr Tyr Val Ala Pro Glu
545                 550                 555                 560

Ile Ile Ala Glu Thr Gly Tyr Gly Leu Lys Val Asp Ile Trp Ala Ala
                565                 570                 575

Gly Val Ile Thr Tyr Ile Leu Leu Cys Gly Phe Pro Pro Phe Arg Ser
            580                 585                 590

Glu Asn Asn Leu Gln Glu Asp Leu Phe Asp Gln Ile Leu Ala Gly Lys
        595                 600                 605

Leu Glu Phe Pro Ala Pro Tyr Trp Asp Asn Ile Thr Asp Ser Ala Lys
        610                 615                 620

Glu Leu Ile Ser Gln Met Leu Gln Val Asn Val Glu Ala Arg Cys Thr
625                 630                 635                 640

Ala Gly Gln Ile Leu Ser His Pro Trp Val Ser Asp Asp Ala Ser Gln
                645                 650                 655

Glu Asn Asn Met Gln Ala Glu Val Thr Gly Lys Leu Lys Gln His Phe
                660                 665                 670

Asn Asn Ala Leu Pro Lys Gln Asn Ser Thr Thr Thr Gly Val Ser Val
            675                 680                 685

Ile Met Asn Thr Ala Leu Asp Lys Glu Gly Gln Ile Phe Cys Ser Lys
        690                 695                 700

His Cys Gln Asp Ser Gly Arg Pro Gly Met Glu Pro Ile Ser Pro Val
705                 710                 715                 720

Pro Pro Ser Val Glu Glu Ile Pro Val Pro Gly Glu Ala Val Pro Ala
                725                 730                 735
```

-continued

```
Pro Thr Pro Pro Glu Ser Pro Thr Pro His Cys Pro Pro Ala Ala Pro
            740                 745                 750
Gly Gly Glu Arg Ala Gly Thr Trp Arg Arg His Arg Asp
            755                 760                 765
```